(12) United States Patent
Sinnreich et al.

(10) Patent No.: US 8,617,182 B1
(45) Date of Patent: Dec. 31, 2013

(54) SURGICAL STAPLE REMOVER

(71) Applicant: Sinn RX, LLC, Miami Beach, FL (US)

(72) Inventors: Matthew Sinnreich, Hollywood, CA (US); William Sinnreich, Boynton Beach, FL (US)

(73) Assignee: Sinn Rx, LLC, Miami ( * ) Notice: Subject to any disclaimer, the term of this patent is extended or adjusted under 35 U.S.C. 154(b) by 0 days.

(21) Appl. No.: 13/769,633

(22) Filed: Feb. 18, 2013

(51) Int. Cl.
*A61B 17/10* (2006.01)

(52) U.S. Cl.
USPC .................................................. 606/138

(58) Field of Classification Search
USPC .......... 227/19, 63, 156; 606/1, 131, 138, 174, 606/205, 206, 207, 208; 81/342, 355, 362; 254/21, 28; 269/3, 6; 29/243.5, 270, 29/278
See application file for complete search history.

(56) References Cited

U.S. PATENT DOCUMENTS

| | | | |
|---|---|---|---|
| 3,819,100 A * | 6/1974 | Noiles et al. .................. 227/19 |
| 4,026,520 A | 5/1977 | Rothfuss et al. |
| 4,073,179 A | 2/1978 | Hickey et al. |
| D271,742 S | 12/1983 | Li et al. |
| 4,487,394 A | 12/1984 | Rothfuss et al. |
| D280,019 S | 8/1985 | Meyer et al. |
| D281,624 S | 12/1985 | Babini |
| D283,048 S | 3/1986 | Sharkany |
| D287,279 S | 12/1986 | Lazickas |
| 4,685,460 A | 8/1987 | Thornton |
| 4,802,614 A * | 2/1989 | Green et al. .................. 227/19 |
| 4,805,876 A | 2/1989 | Blake et al. |
| D302,466 S | 7/1989 | Porat et al. |
| D308,807 S | 6/1990 | Yu |
| 5,116,349 A * | 5/1992 | Aranyi .................. 227/181.1 |
| 5,190,203 A * | 3/1993 | Rodak .................. 227/175.1 |
| 5,236,435 A | 8/1993 | Sewell, Jr. |
| 5,304,185 A * | 4/1994 | Taylor .................. 606/147 |
| 5,364,406 A | 11/1994 | Sewell, Jr. |
| 5,451,231 A | 9/1995 | Rabenau et al. |
| 5,509,596 A * | 4/1996 | Green et al. .................. 227/176.1 |
| 5,938,178 A | 8/1999 | Oh |
| 5,957,430 A | 9/1999 | Olson |
| 6,105,936 A | 8/2000 | Malek |
| D438,965 S | 3/2001 | Porat |
| 6,391,035 B1 | 5/2002 | Appleby et al. |
| 6,513,788 B1 | 2/2003 | Ashe |
| 6,641,114 B1 | 11/2003 | Davis |
| 7,048,255 B2 | 5/2006 | Buch et al. |
| 7,090,198 B1 | 8/2006 | Gurmu |
| 7,131,977 B2 | 11/2006 | Fowler |
| 7,481,824 B2 * | 1/2009 | Boudreaux et al. .......... 606/205 |
| 7,654,431 B2 * | 2/2010 | Hueil et al. .................. 227/175.1 |

(Continued)

*Primary Examiner* — Kathleen Holwerda
*Assistant Examiner* — Jonathan W Miles
(74) *Attorney, Agent, or Firm* — Mark Terry

(57) ABSTRACT

A surgical staple remover apparatus includes a handle located at a rear of the apparatus, an upward sloped jaw element comprising a pair of parallel jaws, an arm having a hook element on a first end, a pivot point located along the arm, such that the arm pivots about the pivot point, a lever coupled to the arm, wherein moving the lever closer to the handle results in the arm pivoting about the pivot point, the hook element moving downwards towards the jaw element and the arm retracting toward the rear, thereby resulting in the hook element pressing against a crown of a surgical staple and moving the surgical staple towards the rear, and a strip element located on top of the jaw element, such that the surgical staple is moved under the strip element and held in place by same.

7 Claims, 11 Drawing Sheets

(56) References Cited

U.S. PATENT DOCUMENTS

| | | | |
|---|---|---|---|
| 7,708,757 B2 * | 5/2010 | Ganter | 606/205 |
| RE43,049 E * | 12/2011 | Grace | 606/208 |
| 8,177,793 B2 | 5/2012 | Sinnreich | |
| 8,241,303 B2 | 8/2012 | Sinnreich | |
| 2004/0249411 A1 * | 12/2004 | Suzuki | 606/205 |
| 2006/0047304 A1 * | 3/2006 | Ganter | 606/205 |

* cited by examiner

SURGICAL STAPLE REMOVER

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of medical devices, and more particularly relates to the field of devices for automating the process of removing surgical staples.

BACKGROUND OF THE INVENTION

The use of surgical staples in the medical industry for closing wounds or incisions in the skin of a patient has grown over the last decade due to its advantages over thread sutures. One of the main advantages of surgical staples over thread sutures is the reduced amount of time required for surgical staples to be implanted. In cases where large incisions are made, the use of surgical staples can, for example, reduce the length of time required for the suturing process and thus the length of time the patient must be maintained under anesthesia.

Conventional surgical staples comprise an elongated crown and an L-shaped portion on each end of the crown, wherein when implanted in a patient, the crown is located on the exterior of the skin of the patient and the L-shaped portions are bent in a downward direction so that the ends of the L-shaped portions are opposed, thereby incising and gripping the skin. The aforementioned conventional surgical staple may be removed from the skin of a patient by deforming the staple crown into a U-shaped configuration. This causes the L-shaped legs of the staple to shift upwardly and outwardly so that they may be lifted away from the patient's skin.

A conventional surgical staple remover 1, shown in FIG. 1, typically comprises a first handle 2 and a second handle 3 pivoted together at pivot point 11. Each handle includes circular finger inserts (4 and 5), each of which includes an orifice (6 and 7) for inserting a pair of fingers, such as a thumb and forefinger. The second handle 3 terminates in element 8 comprising two parallel, dual-pronged J-shaped units that are inserted under a surgical staple to be removed. The first handle 2 terminates in an anvil 10 that includes a downward facing footprint that is situated between the two units of the dual-pronged J-shaped element 8 and wherein the anvil 10 is placed on top of the crown of the surgical staple to be removed. When the conventional surgical staple remover 1 is gripped and contracted by a user, the downward facing footprint of anvil 10 applies force to the top of the crown of the surgical staple, thereby deforming the staple crown into a U-shaped configuration. Consequently, the L-shaped legs of the staple are moved upwardly and outwardly, thereby lifting away from the patient's skin.

One of the disadvantages of a conventional surgical staple remover is that it does not adequately deal with the final disposition of the surgical staple being removed. It is common to have surgical staples jump into the air or fall away during removal. Personnel must then go about finding and disposing of the removed surgical staple and sterilizing anything the staple came into contact with. It is unsanitary to allow removed surgical staples to come into contact with individuals or things since implanted surgical staples have resided within a human's body and may contain biologically hazardous residue that could contaminate individuals and locations. Further, the process of cleaning up after the conventional removal of surgical staples is time consuming and expensive since proper decontamination and sterilization procedures, employing the use of costly protective equipment and cleaning materials, must be undertaken. Further, during an operation on a patient, it is imperative that all removed staples are accounted for, lest the removed staple falls into an open incision unnoticed.

Another disadvantage of a conventional surgical staple remover is that it requires that each removed surgical staple is immediately disposed of. That is, the doctor or technician must remove a surgical staple, place it in a receptacle, and then return to the wound to remove the next surgical staple. This is problematic as it requires that the doctor or technician temporarily lose sight of the wound while he disposes of the removed surgical staple.

Therefore, a need exists to overcome the problems with the prior art as discussed above, and particularly for a more effective and efficient surgical staple remover, as well as a more sanitary and easy-to-operate surgical staple remover.

SUMMARY OF THE INVENTION

Briefly, according to an embodiment, a surgical staple remover apparatus is disclosed. The surgical staple remover apparatus comprises a handle located at a rear of the apparatus, an upward sloped jaw element comprising a pair of parallel jaws, an arm having a hook element on a first end, wherein the arm is positioned such that the hook element is disposed over the jaw element, a pivot point located between the first end and a second end of the arm, such that the arm pivots about the pivot point, and a lever mechanically coupled to the arm, wherein moving the lever closer to the handle results in the arm pivoting about the pivot point, the hook element moving downwards towards the jaw element and the arm retracting toward the rear, thereby resulting in the hook element pressing against a crown of a surgical staple, deforming the surgical staple for removal and moving the surgical staple towards the rear. The surgical staple remover apparatus further includes a strip element located on top of the jaw element, such that when the hook element deforms and moves the surgical staple towards the rear, the surgical staple is moved under the strip element and held in place by same.

The foregoing and other features and advantages of the embodiments will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

DETAILED DESCRIPTION

Applicant's surgical staple remover solves problems with the prior art by providing a simple and easy-to-use surgical staple remover that automatically captures deformed and removed surgical staples. The surgical staple remover apparatus improves upon the prior art by definitively dealing with the final disposition of each surgical staple being removed from a patient. The surgical staple remover apparatus eliminates the possibility of having surgical staples jump into the air or fall away during removal. The surgical staple remover apparatus further eliminates the necessity for personnel to find and dispose of the removed surgical staple and sterilize anything the staple came into contact with. The surgical staple remover apparatus eradicates the potential for removed surgical staples to come into contact with, and contaminating, individuals or things. Further, the surgical staple remover apparatus eliminates the need to clean up after the conventional removal of surgical staples, thereby saving time and expense. Also, the surgical staple remover apparatus allows a doctor or technician to undergo the process of removing multiple surgical staples without losing sight of the wound during the process.

Finally, the surgical staple remover apparatus provides a surgical staple remover with a minimal number of component parts, thereby reducing the potential for failure or malfunction of the device. Also, the minimal number of component parts allows for quick and inexpensive fabrication of the surgical staple remover, thereby meeting the economic requirements for a disposable surgical staple remover. The surgical staple remover apparatus can be constructed of various metals, as well as plastic.

Figure 1:
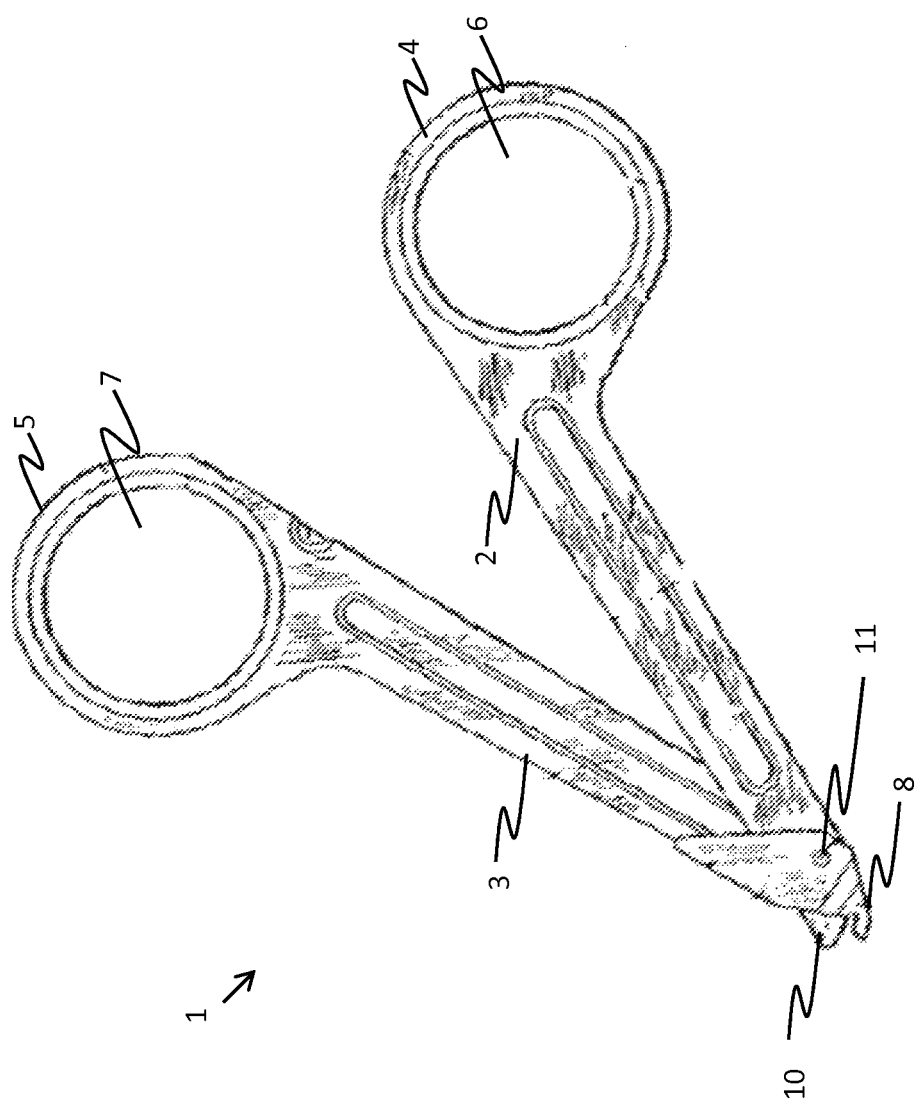
FIG. 1 is an illustration of a side view of a prior art surgical staple remover.
Figure 2A:
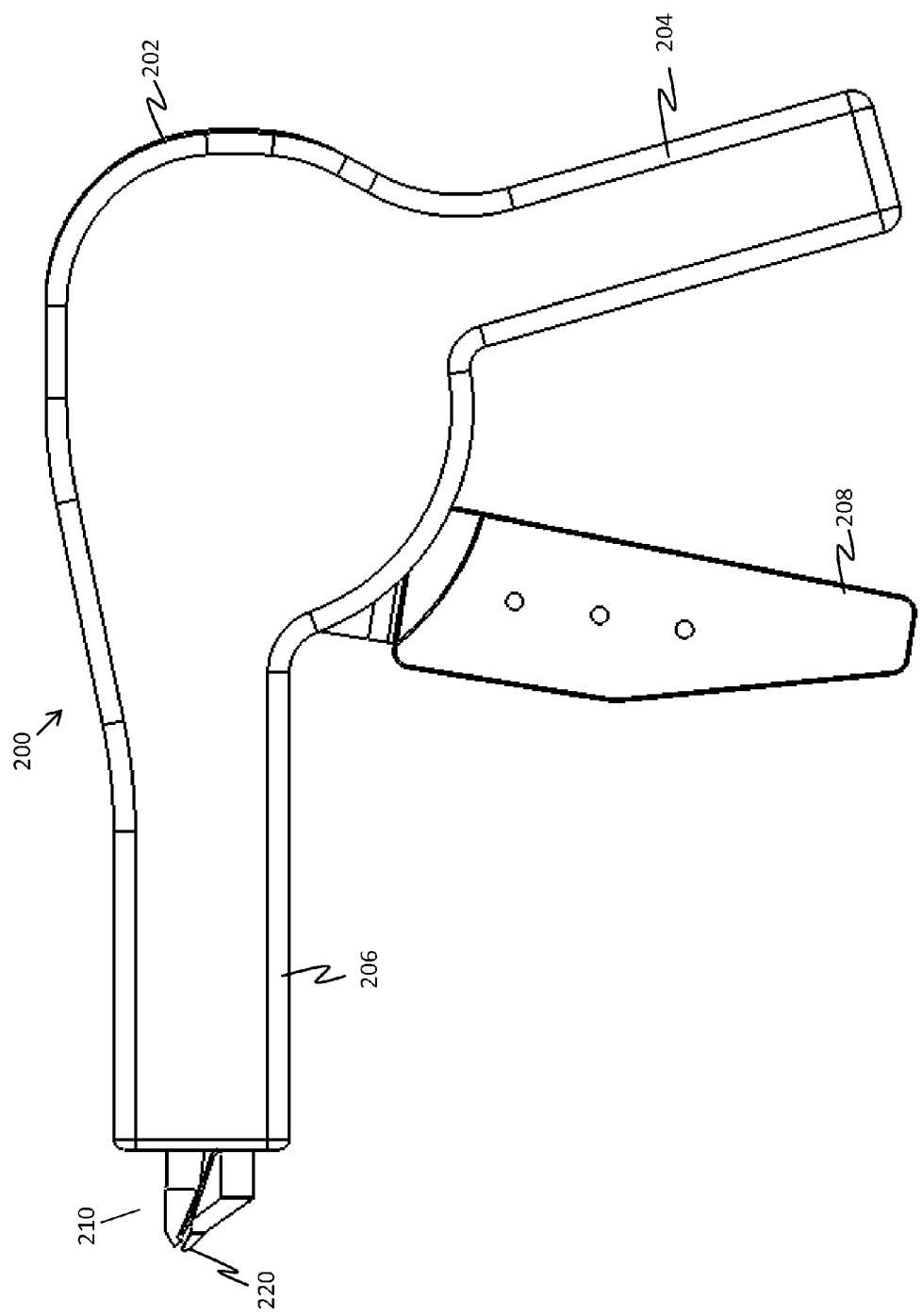
FIG. 2A is a left side view of the surgical staple remover in an open position, in accordance with one embodiment.

The embodiments of the surgical staple remover apparatus will be described heretofore with reference to FIGS. 2A through 6 below. FIG. 2A is a left side view of the surgical staple remover 200 in an open position, in accordance with one embodiment. The apparatus 200 may be composed of a conventional medical device material such as stainless steel and other metal alloys, or a disposable material, such as plastic or a plastic derivative, so that the apparatus may be disposed after a single use, thereby eliminating the necessity for cleaning or sterilizing the apparatus between uses. One or more of the components that comprise the apparatus 200 may be stamp manufactured from a planar metallic sheet or molded from plastic using conventional plastic molding processes. See FIG. 6 which shows an exploded view of the components of the surgical staple remover 200. The low number of parts, especially moving parts, and the simplicity of the design results in a surgical staple remover 200 that is straightforward and inexpensive to fabricate, thereby meeting the requirements for a disposable medical device.

The apparatus 200 may include a body or housing 202 that comprises a handle 204 (for accommodating the palm of a user's hand) and a protruding element 206 that includes the working end 210 of the surgical staple remover, for removing and capturing staples, such as staple 220. The apparatus 200 may also include a lever 208 (for accommodating one or more of the user's fingers) that rotates about a pivot point when pressed such that the lever 208 moves closer to the handle 204, i.e., towards the rear of the apparatus 200 or proximally. (The lever 208 may have two covers 602, 604 shown in the exploded view of FIG. 6.) Note that the angle between the handle 204 and the lever 208 may be substantially in the range of thirty degrees and ninety degrees. Thus, operation of the apparatus 200 occurs as follows: the user holds the apparatus 200 via the handle 204, the jaw element of the working end 210 is placed under the staple 200, the lever 208 is pressed by the user's fingers so as to move the lever 208 closer to the handle 204, i.e., proximally, and the working end 210 of the apparatus 200 deforms the staple 220, removes it, and retracts the staple 220 towards the rear of the apparatus 200 or proximally.

Figure 2B:
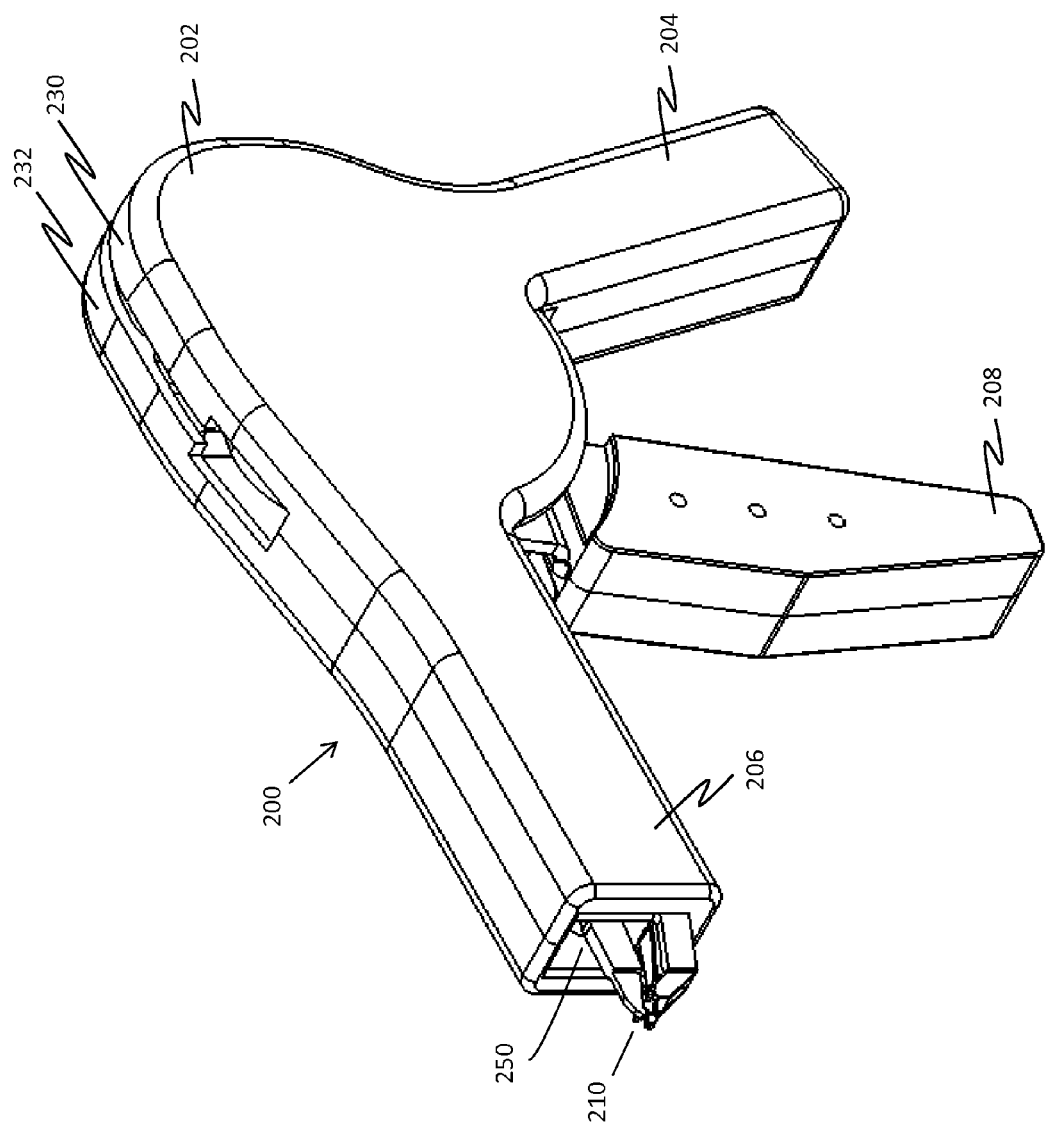
FIG. 2B is a perspective view of the surgical staple remover in a closed position, in accordance with one embodiment.

FIG. 2B is a perspective view of the surgical staple remover 200 in a closed position, showing that the working end of the surgical staple remover 200 has removed the staple 220 and secured it. FIG. 2B further shows that the body or housing 202 of the surgical staple remover 200 may comprise two parts 230, 232, wherein each part comprises one half of the entire housing 202, having an interior volume that encompasses various interior working components of the apparatus 200. The two parts 230, 232 of the housing 202 may be coupled via one or more screws, tabs, or other fasteners. FIG. 2B shows that the protruding element 206 of housing 202 includes an opening 250 that provides access to the interior volume of the housing 202 and from which portions or components of the working end 210 of apparatus 200 project.

Figure 3:
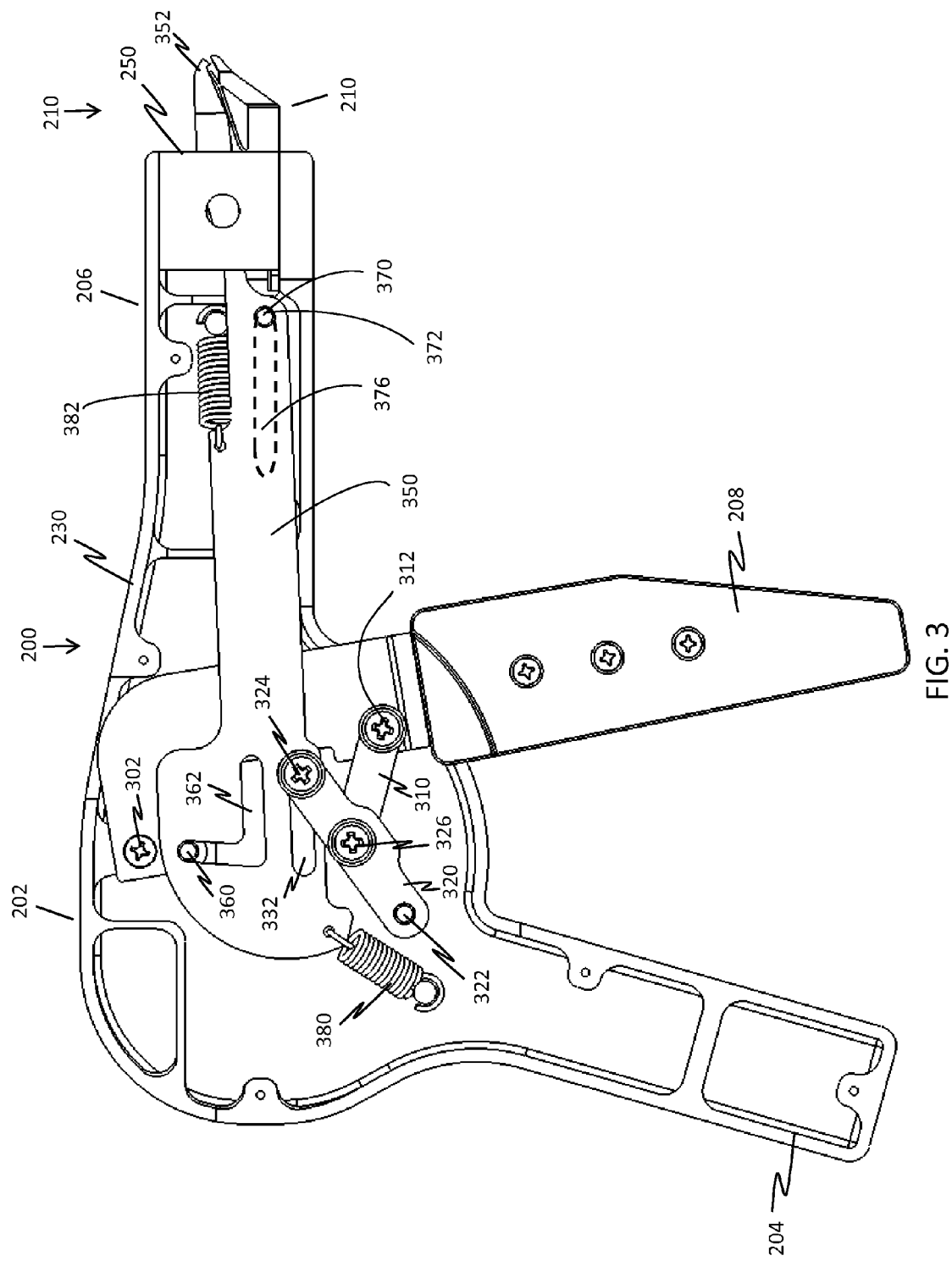
FIG. 3 is a right side view of the surgical staple remover in an open position, in accordance with one embodiment.

FIG. 3 is a right side view of the surgical staple remover 200 in an open position, in accordance with one embodiment. FIG. 3 shows one view of the apparatus 200 wherein the part 232 of the housing 202 has been removed such that the interior components of the apparatus 200 may be viewed. FIG. 3 shows that the lever 208 is pivotally or rotatably connected to the part 230 of housing 202 at pivot point 302 such that the lever 208 rotates or pivots about the pivot point 302. A pivot point is point wherein a first element is attached to a second element and wherein the first element may pivot or rotate about the pivot point. A pivot point may, for example, include a screw, shaft, hinge or other attachment mechanism that both attaches the first element to the second element but that still allows the first element to pivot or rotate. FIG. 3 also shows that a rigid first beam 310 is rotatably connected to lever 208 at pivot point 312 such that first beam 310 rotates with respect to the lever 208 about the pivot point 312. The pivot point 312 is located at a first end of first beam 310. Another pivot point 326 is located at the second end of first beam 310.

In this document, the terms pivotally or rotatably connected or coupled refers to a first element being attached to a second element in such a way that the first element and/or the second element may rotate or pivot in relation to the other element. The attachment mechanism between the first and second elements may be a hinge, socket, joint, gate or the like. Also, the term mechanically connected or coupled refers to a first element being either directly to indirectly attached to a second element using mechanical means. For example, lever 208 is mechanically coupled to arm 350, since beams 310 and 320 provide the connection between lever 208 and arm 350.

FIG. 3 also shows a rigid second beam 320 having a first end, a second end and a midpoint. The first end of second beam 320 is rotatably connected to part 230 at pivot point 322 such that the second beam 320 rotates about the pivot point 322. The midpoint of second beam 320 is rotatably connected to first beam 310 at pivot point 326 such that the first beam 310 and second beam 320 rotate with respect to each other about the pivot point 326. Note that pivot point 326 may be located in any location on second beam 320 between the first and second ends of the second beam 320. Note that the pivot points 302, 312, 326 and 322 may comprise pin and bore embodiments, wherein an orifice or bore is located in one or both elements of the pivot point, and a pin or shaft extends through the bore. In one embodiment, the aforementioned pivot points include a bore, a pin comprising a screw and one or more washers to facilitate the rotation of one or both elements about the screw.

The apparatus 200 also includes an arm 350, which comprises a planar element that extends from the interior of the housing 202, through the protruding element 206 and extending out of the opening 250. The arm 350 includes a hook element 352 at a distal end, wherein the hook element 352 comprises a hook shaped element that protrudes downwards from the arm 350. The downward facing hook element 350 includes a footprint for placement on top of a crown of a surgical staple. The hook element 350 serves to hook or grab the removed surgical staple as it is retracted towards the rear of the apparatus 200, or proximally.

FIG. 3 shows the second end of second beam 320 is rotatably connected to arm 350 at pivot point 324 such that the second beam 320 and arm 350 rotate with respect to each other about the pivot point 324. In one embodiment, the pivot point 324 may comprise a sliding or dynamic pivot point wherein the location of the pivot point in arm 350 is not fixed. In this embodiment, the pivot point 324 may comprise a channel or cutout 332 in the arm 350. A channel or cutout is a portion of a planar element that has been removed so as to present a gutter or conduit carved out of a surface of the arm 350 or, alternatively, an aperture or orifice of various sizes in the surface of the arm 350. In this embodiment, the pivot point 324 may comprise a pin, rod or shaft that is fixed or secured to the second beam 320 and that extends into or through the channel or cutout 332. As the second beam 320 moves in relation to the arm 350, the second end of second beam 320 (i.e., pivot point 324) moves in the path defined by the channel or cutout 332. The purpose of channel or cutout 332 is to define the movement of the arm 350 in response to the movement of the pivot point 324 due to the rotation of the second beam 320.

In one embodiment, the channel or cutout 332 may extend substantially horizontally in a substantially straight line along the main longitudinal axis of the arm 350, allowing for insertion of the pin, rod or shaft of the second beam 320. In this embodiment, the channel or cutout 332 may have an elongated form with rounded edges.

FIG. 3 also shows that arm 350 includes a channel or cutout 362, which may extend substantially horizontally in a substantially straight line along the main longitudinal axis of the arm 350, allowing for insertion of a pin, rod or shaft 360, which is affixed or secured to (i.e., stationary with respect to) housing 202 and/or parts 230, 232. In another embodiment, the channel or cutout 362 also has a portion extending substantially vertically in a substantially straight line, thereby having substantially an L-shape. The pin, rod or shaft 360 is inserted into the channel or cutout 362 and thus the arm 350 follows the path of the channel or cutout 362 when the arm 350 moves in relation to the housing 202. The purpose of cutout 362 is to define the movement of the arm 350 in relation to the housing 202.

FIG. 3 further shows that housing 202 includes a channel or cutout 376 located between the working end 210 and the rear or proximal end of the apparatus 200. FIG. 3 also shows a pivot point 372, which comprises a pin, rod or shaft 370 that is secured to the arm 350 such that it is stationary with respect the arm 350. The channel or cutout 376 extends substantially horizontally in a substantially straight line along the main longitudinal axis of the protruding element 206 of housing 202, wherein the cutout 376 allows for insertion of the pin, rod or shaft 370 of the arm 350. The pin, rod or shaft of arm 350 is inserted into the cutout 376 and thus the arm 350 follows the path of the cutout 376 when the arm 350 moves in relation to the housing 202. The purpose of cutout 376 is to define the movement of the arm 350 in relation to the housing 202. Furthermore, the pivot point 372 acts as a pivot about which arm 350 rotates when the arm 350 moves in relation to the housing 202. The pivot point 372 acts like a fulcrum wherein when the left side of the arm 350 move upwards, the right side of the arm 350 moves downwards, and vice versa.

Lastly, FIG. 3 shows a first spring 380 that is attached to the arm 350 at a top end and attached to the housing 202 at a bottom end. Thus, the bottom end of the spring 380 is stationary with respect to the housing 202. The spring 380 provides a downward force upon arm 350 as the arm 350 moves upwards and away from the spring 380. FIG. 3 also shows a second spring 382 that is attached to the arm 350 at a proximal end and attached to the housing 202 at a distal end. Thus, the distal end of the spring 382 is stationary with respect to the housing 202. The spring 382 provides a distal or outward force upon arm 350 as the arm 350 moves inwards or proximally into the apparatus 200.

Figure 4A:
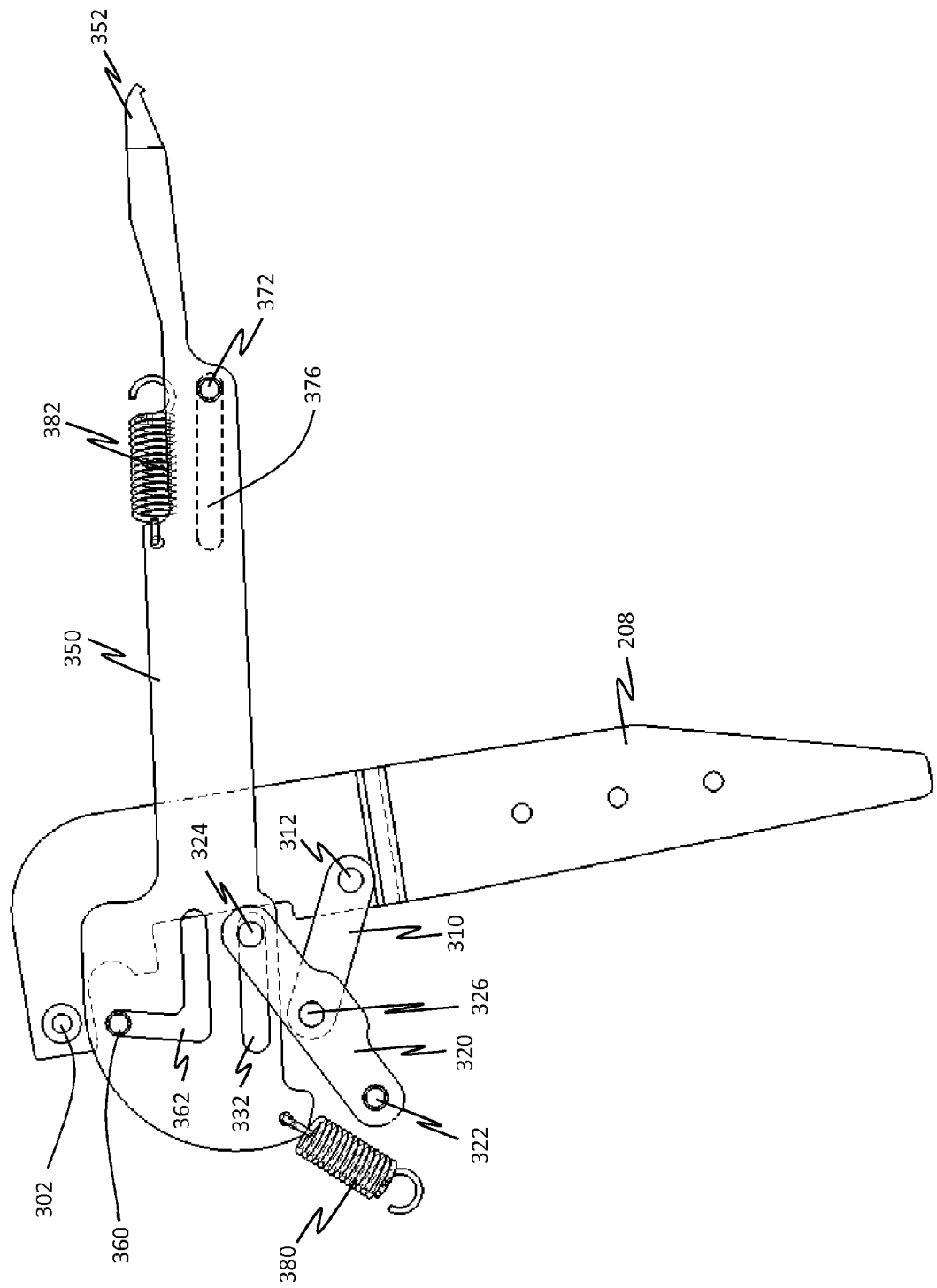
FIG. 4A is a right side view of the moving interior components of the surgical staple remover in an open position, in accordance with one embodiment.

FIG. 4A is a right side view of the moving interior components of the surgical staple remover 200 in an open position, in accordance with one embodiment. The open position corresponds to a position wherein the apparatus 200 is not in use or has not been activated by a user. In the open position, the lever 208 and the arm 350 are positioned as far forward as the apparatus 200 allows. Further, springs 380 and 382 have not been extended, or fully extended, and therefore the forces provided by the springs 380 and 382 upon the arm 350 are minimal or nonexistent.

Figure 4B:
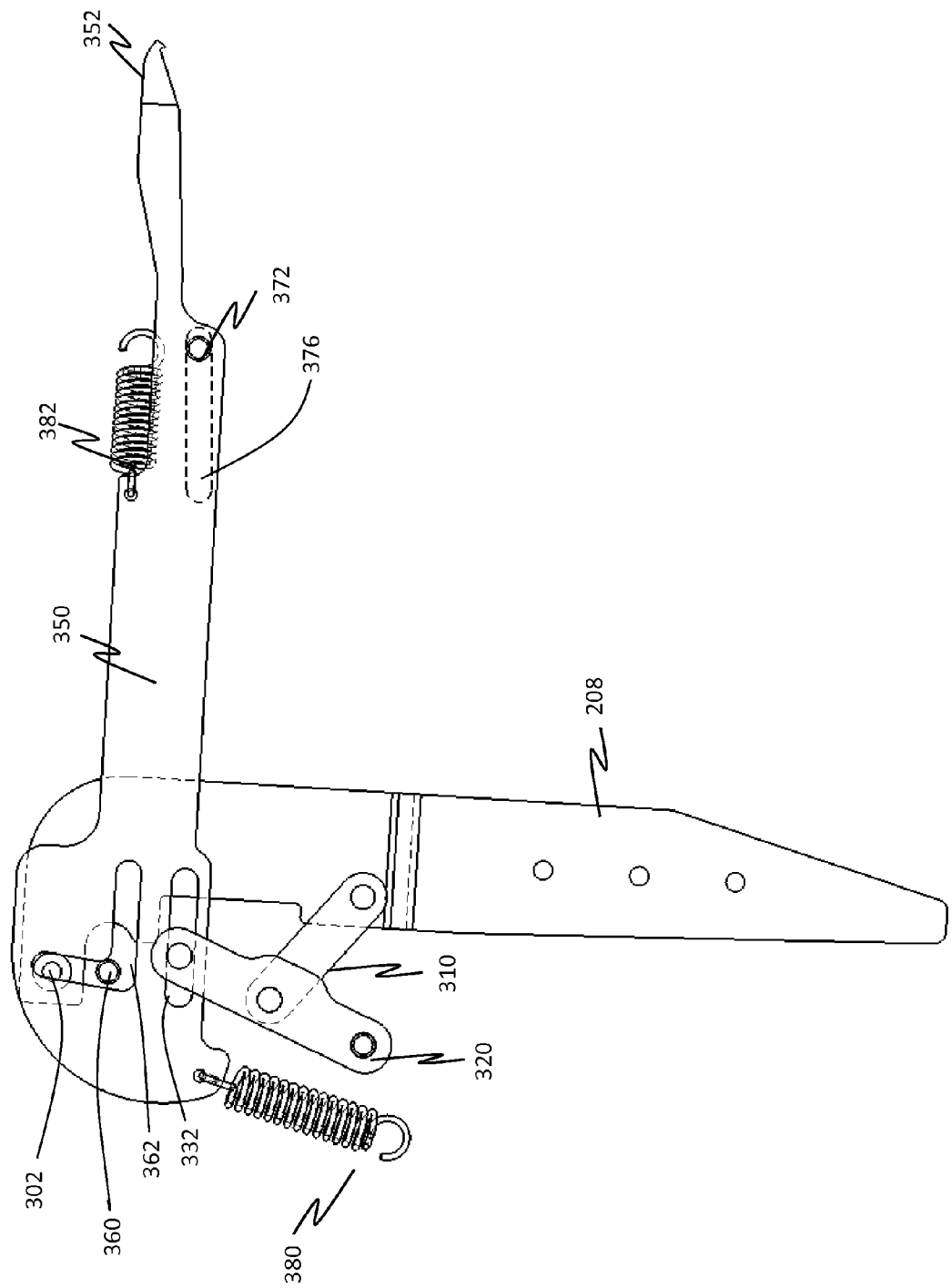
FIG. 4B is a right side view of the moving interior components of the surgical staple remover in an interim position, in accordance with one embodiment.

FIG. 4B is a right side view of the moving interior components of the surgical staple remover 200 in an interim position, in accordance with one embodiment. The interim position corresponds to a position wherein the apparatus 200 is in use and has been partially activated by a user while removing a surgical staple. Specifically, the interim position corresponds to a state of use wherein the lever 208 has been pulled back by a user to approximately half or 50 percent of its range of motion. In the interim position, the lever 208 and the arm 350 have been moved towards the rear of the apparatus 200, or proximally, approximately half or 50 percent of the distance allowed by the apparatus 200. Further, springs 380 and 382 have been partially extended, and therefore the spring 380 provides a stronger downward force upon arm 350 and spring 382 provides a stronger distal or outward force upon arm 350.

FIG. 4B shows that as lever 208 has been pulled back towards the rear or apparatus 200, the lever 208 has rotated about pivot point 302 such that lever 208 is closer to the vertical of FIG. 4B. Further, lever 208 has pushed first beam 310 such that the first beam 310 is at substantially a forty-five degree angle with the horizontal of FIG. 4B. Also, first beam 310 has pushed second beam 320 such that second beam 320 is closer to the vertical of FIG. 4B. Note also that the angle between the first beam 310 and the second beam 320 has changed. Whereas in FIG. 4A, an acute angle is made between the vertices 312, 326 and 324, in FIG. 4B, the relationship between the first beam 310 and the second beam 320 has changed such that an obtuse angle is made between the vertices 312, 326 and 324.

FIG. 4B also shows that as second beam 320 has rotated, the pivot point 324 has traveled substantially to the rear-most/left-most portion of the cutout 332. Further, as the second beam 320 has rotated such that the pivot point 324 has traveled upwards, due to the interaction of the pivot point 324 with the cutout 332, the rear portion of the arm 350 has moved upwards. Consequently, due to the role played by the pivot point 372 as a fulcrum, as the rear portion of the arm 350 has moved upwards, the front or distal portion of the arm 350 (i.e., the hook element 352) has moved downwards.

FIG. 4B further shows that as the rear portion of the arm 350 has moved upwards, the pivot point 360 has traveled downwards towards the vertex of the L-shaped cutout 362, or the rear-most/left-most portion of the cutout 362. Lastly, FIG. 4B shows that as the arm 350 has moved towards the rear of the apparatus 200, i.e., proximally, the pivot point 372 has travelled proximally towards the rear of the cutout 376.

Figure 4C:
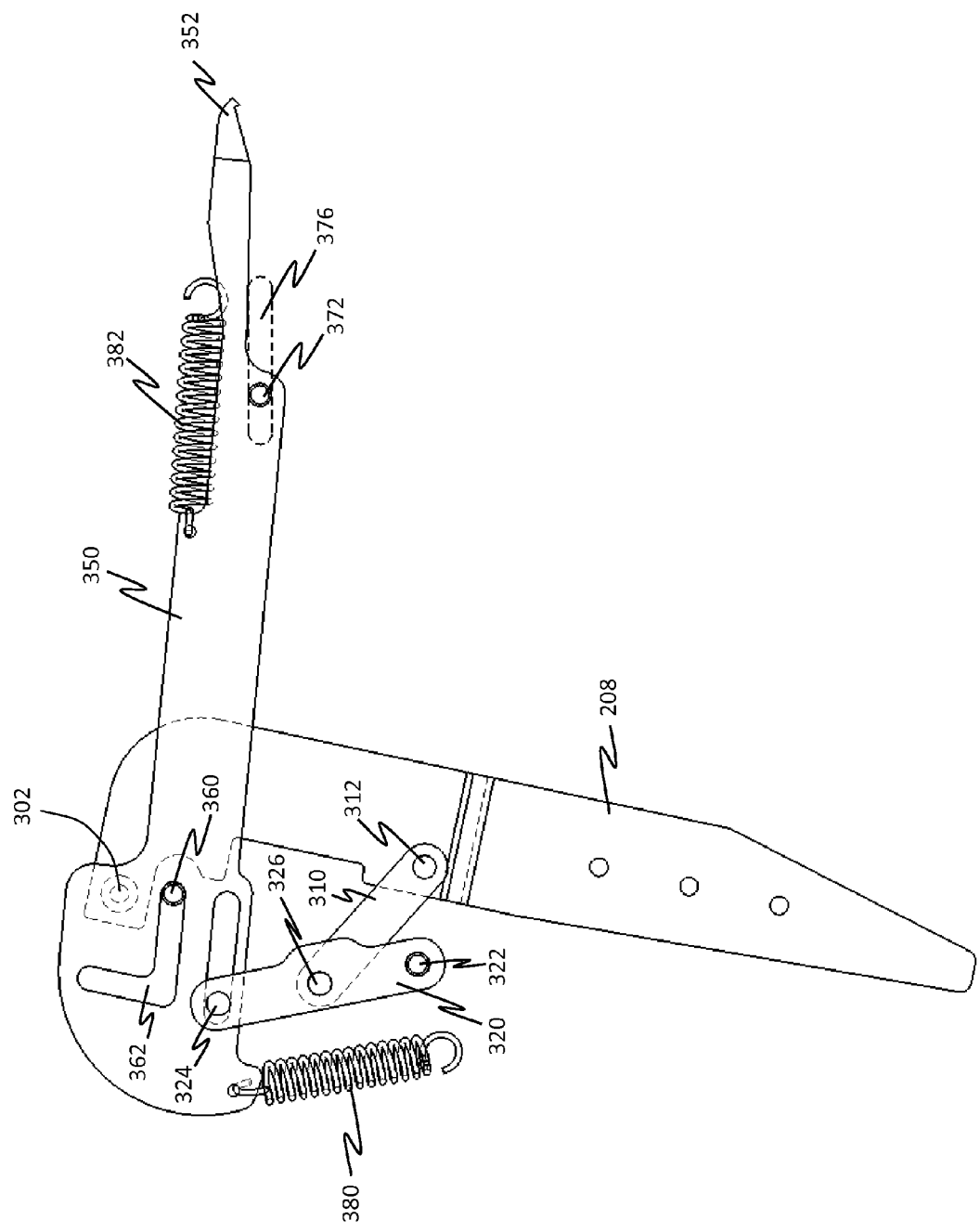
FIG. 4C is a right side view of the moving interior components of the surgical staple remover in a closed position, in accordance with one embodiment.

FIG. 4C is a right side view of the moving interior components of the surgical staple remover 200 in a closed position, in accordance with one embodiment. Specifically, the closed position corresponds to a state of use wherein the lever 208 has been pulled back by a user to the fullest or 100 percent of its range of motion. In the closed position, the lever 208 and the arm 350 have been moved to the rear of the apparatus 200 as far back as allowed by the apparatus 200. Further, springs 380 and 382 have been fully extended, and therefore the spring 380 provides the fullest extent of its downward force upon arm 350 and spring 382 provides the fullest extent distal or outward force upon arm 350.

FIG. 4C shows that as lever 208 has been pulled back towards the rear or apparatus 200, the lever 208 has rotated about pivot point 302 such that lever 208 is substantially parallel to the handle 204. Further, first beam 310 has pushed second beam 320 such that the angle between the first beam 310 and the second beam 320 (i.e., the angle made between the vertices 312, 326 and 322) is smaller or more acute than the same angle in FIG. 4B. Further, the angle made between the vertices 312, 326 and 324 in FIG. 4C is closer to 180 degrees than the same angle made in FIG. 4B.

FIG. 4C also shows that as second beam 320 has rotated, the pivot point 324 remains substantially at the rear-most or left-most portion of the cutout 332. Further, as the arm 350 has moved towards the rear of apparatus 200, the pivot point 360 has traveled forwards towards the forward-most or right-most portion of the cutout 362. Lastly, FIG. 4C show that as the arm 350 has moved towards the rear of the apparatus 200, the pivot point 372 has traveled towards the rear-most or left-most portion of the cutout 376.

Figure 5A:
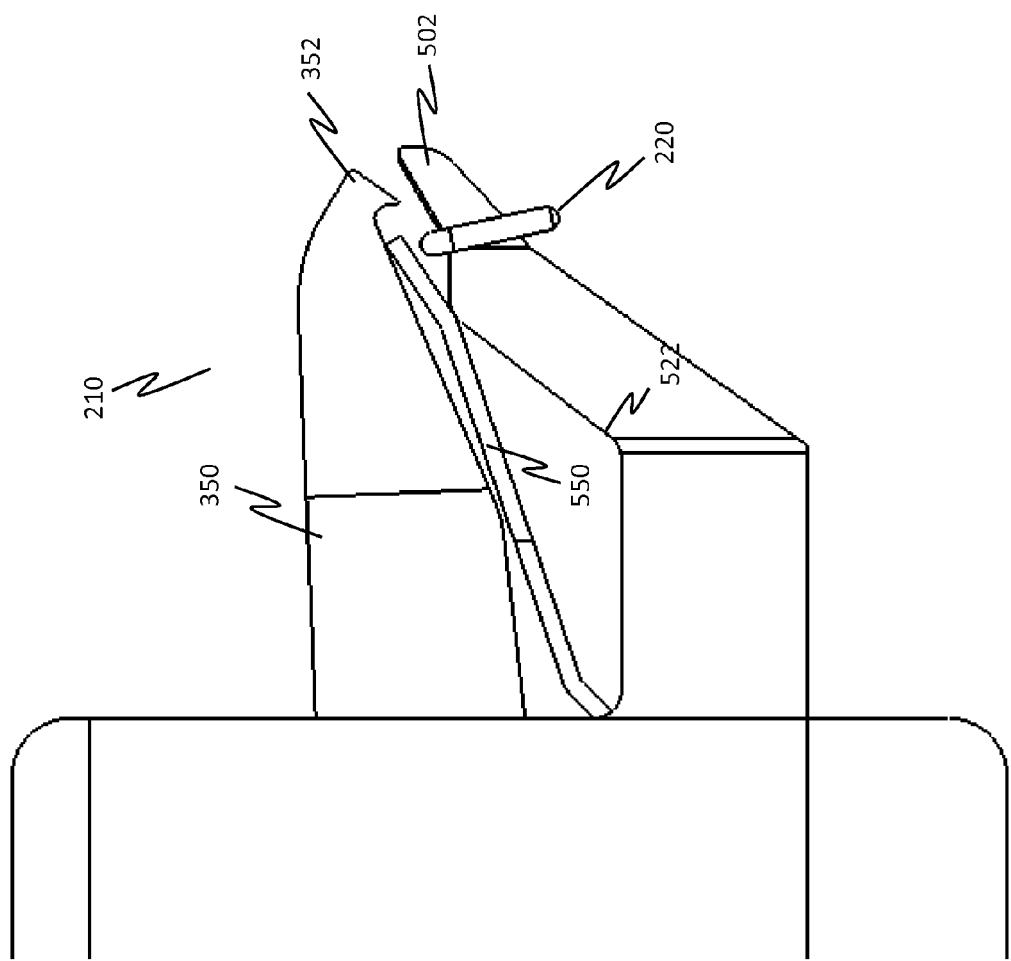
FIG. 5A is a right side view of the components of the working end of the surgical staple remover in an open position, in accordance with one embodiment.
Figure 5B:
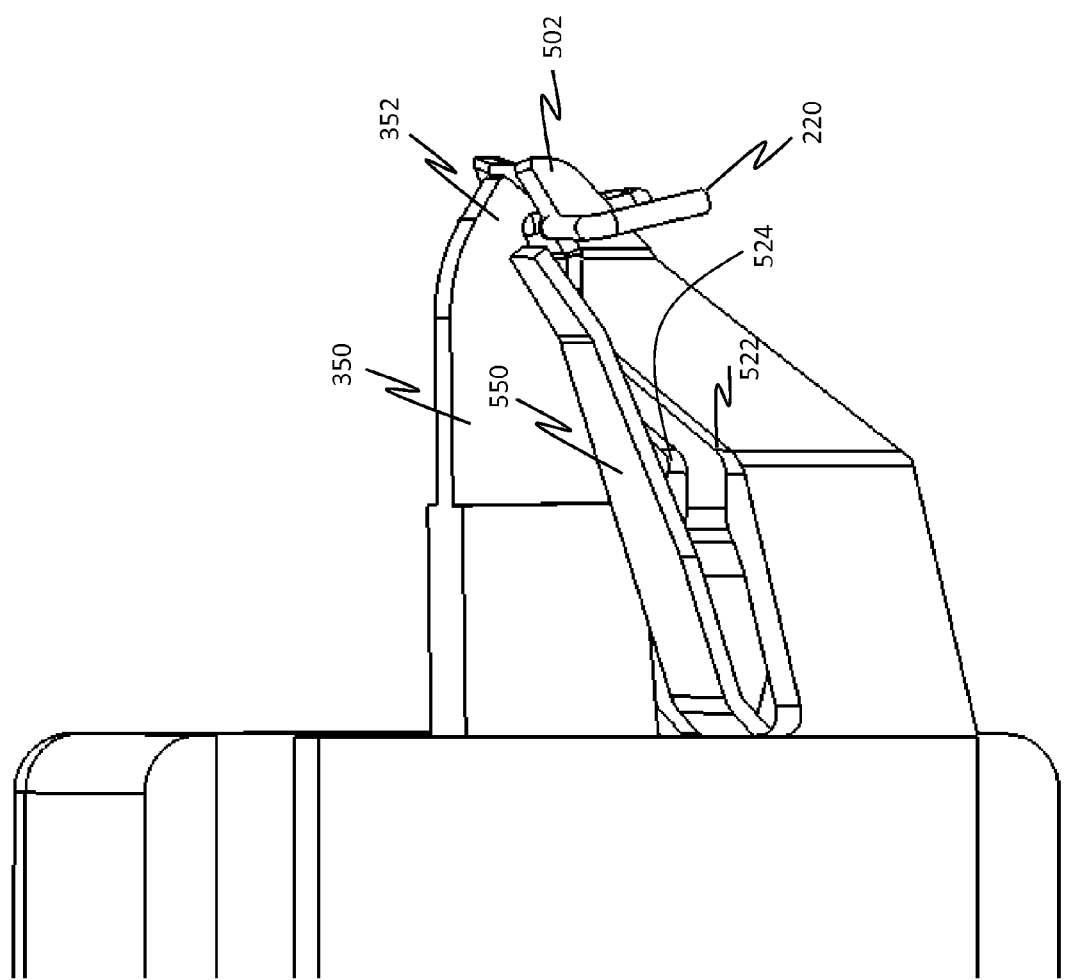
FIG. 5B is a right side view of the components of the working end of the surgical staple remover in an interim position, in accordance with one embodiment.
Figure 5C:
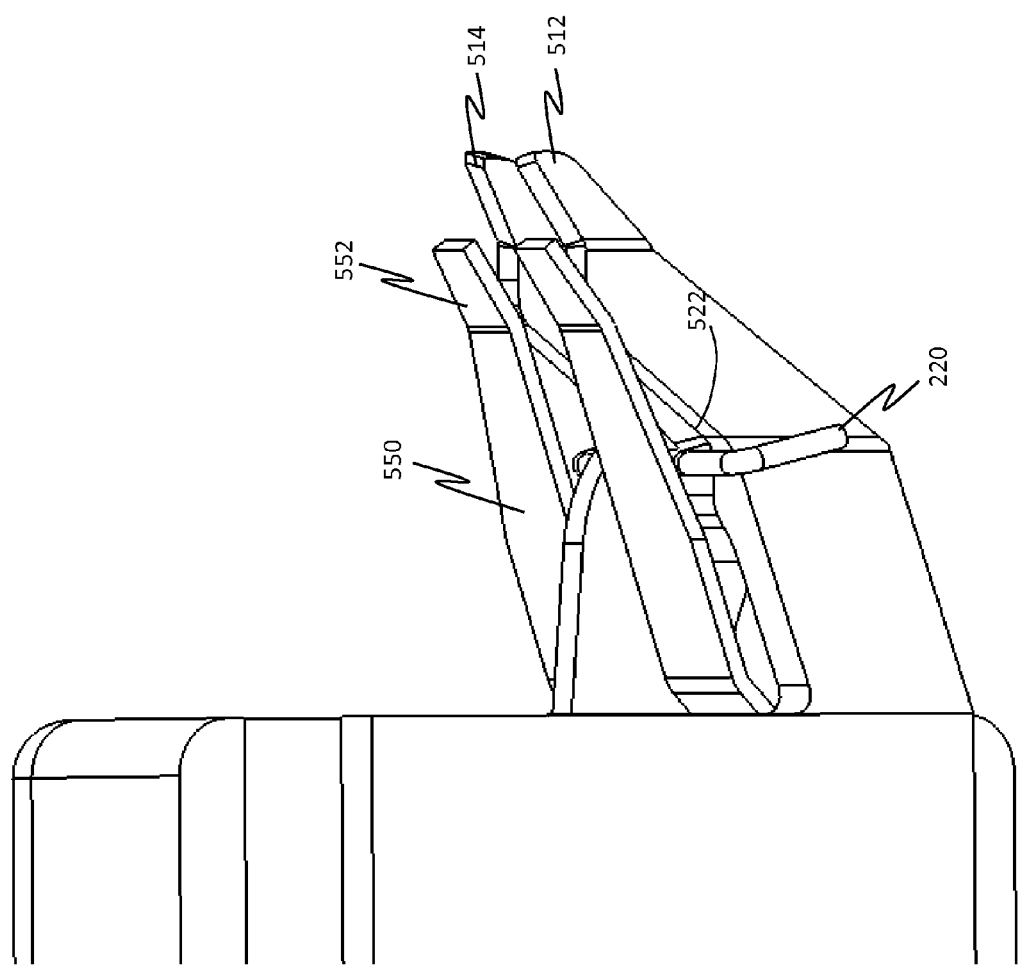
FIG. 5C is a right side view of the components of the working end of the surgical staple remover in a closed position, in accordance with one embodiment.
Figure 6:
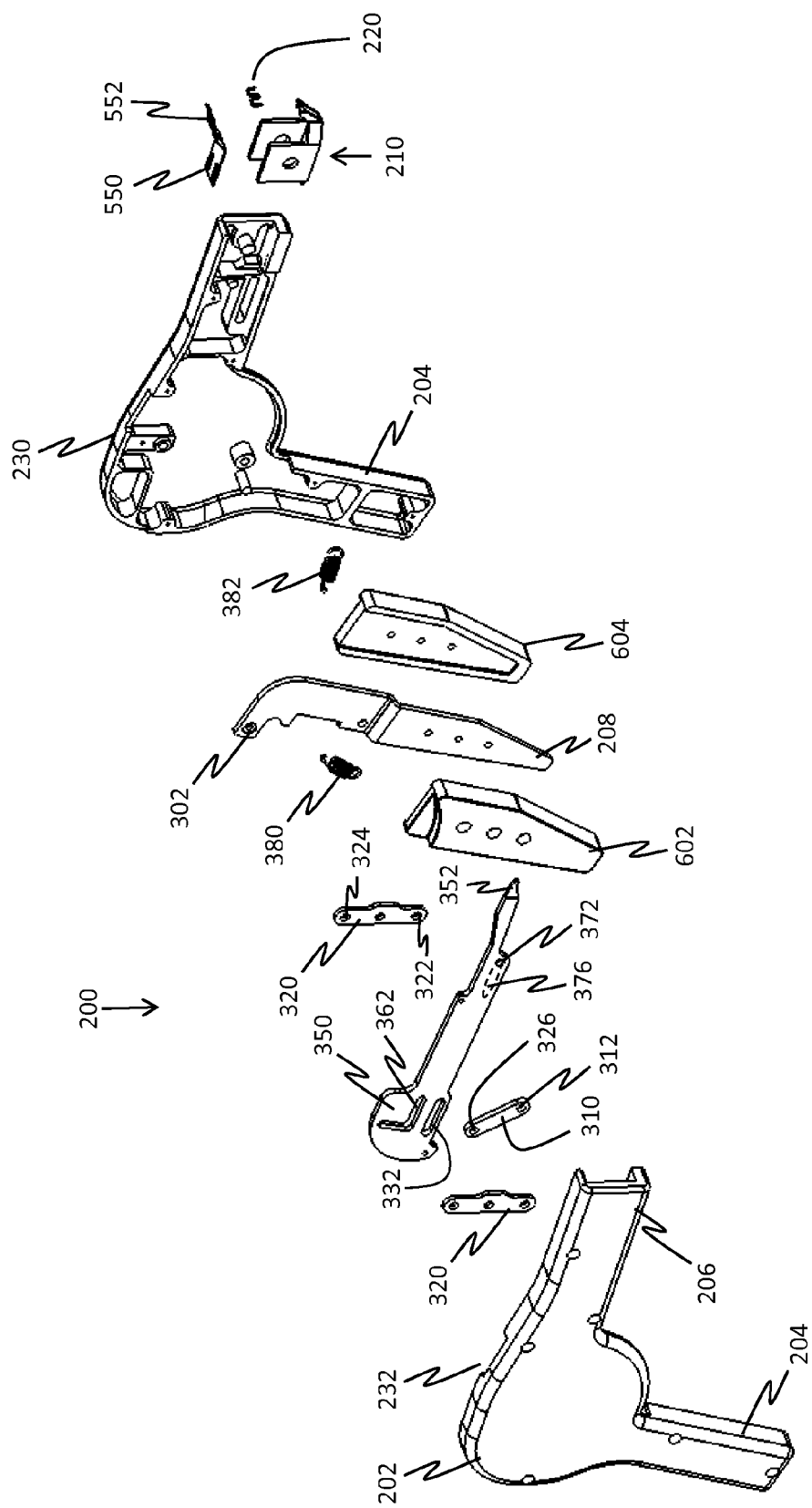
FIG. 6 is an exploded view of the surgical staple remover showing the main interior and exterior components, in accordance with one embodiment.

FIG. 5A is a right side view of the components of the working end 210 of the surgical staple remover 200 in the open position, while FIG. 5B is a right side view (with a slightly angled perspective) of the components of the working end 210 in the interim position, and FIG. 5C is a right side view (with a slightly more angled perspective) of the components in the closed position.

The working end 210 of the surgical staple remover 200 includes a dual-toothed jaw element 502 protruding from the bottom portion of the working end 210 of the surgical staple remover 200 (see FIGS. 5A through 5C). The dual-toothed jaw element 502 may be integrally formed (such as via a stamping process) from one continuous piece of plastic, metal or alloy (or the like). The dual-toothed jaw element 502 includes two parallel jaws 512 and 514 that point in an upward direction. The top surface of the jaws 512 and 514 includes a dip or indentation 522, 524 in which a surgical staple 220 is secured while it is deformed during removal. The dual-toothed jaw element 502 may have a size and shape that allows its insertion underneath a crown of a conventional surgical staple 220. The dual-toothed jaw element 502 may further be engineered to allow for slight lateral expansion to ease the deforming of the surgical staple.

Recall the arm 350 includes a downward facing hook element 352, which may comprise a curved element that protrudes downward from one end of the arm 350, the tip of which includes a footprint for placement on top of a crown of a surgical staple. The hook element 352 serves to hook or grab the removed staple as it is retracted towards or into the opening 250 of the apparatus 200. The gap between the two parallel jaws 512 and 514 of jaw element 502 corresponds to, or accommodates, a profile of the hook element 352 (see FIG. 5B and FIG. 5C).

The hook element 352 and jaw element 502 work in concert to remove surgical staples. At rest, the hook element 352 is separated from the jaw element 502 so as to produce a space between the two items (see the open position of FIG. 5A). The apparatus 200 is maneuvered such that the jaw element 502 is placed underneath the crown of the surgical staple to be removed. The crown of the surgical staple to be removed rests on top of the jaws 512 and 514. Upon retraction the arm 350, the hook element 352 is moved downward towards the jaw element 502 and is eventually moved in between the jaws 512 and 514 of the jaw element 502 (see the interim position of FIG. 5B). In so doing, the hook element 352 deforms the crown of the surgical staple such that the staple crown is bent into a U-shaped configuration, causing the L-shaped legs of the staple to shift upwardly and outwardly so that they may be lifted away from the patient's skin. Subsequently, upon full retraction of the arm 350, the hook element 352 grabs the deformed and removed surgical staple and moves it underneath strip element 550 and in the direction of the rear of apparatus 200, i.e., proximally (see the closed position of FIG. 5C).

FIG. 5C shows that strip element 550 includes dual pronged jaw element 552, which mirrors the jaw element 502, such that jaw element 552 is curved upwards. FIG. 5C shows that the strip element 550 is located on top of jaw element 502 such that there is a narrow space between jaw element 502 and strip element 550 to allow the removed and deformed staple to be held securely in the removal and storage process. When the hook element 352 moves a removed surgical staple towards the opening 250, the removed surgical staple is moved under the strip element 550 and held in place between the jaw element 502 and strip element 550. The strip element 550 may comprise a strip of a shape memory alloy that includes one or more bends. The strip element 550 may hold a plurality of removed surgical staples in between the narrow gap between the element 550 and jaw element 502. In this manner, multiple surgical staples can be quickly and easily removed, and securely captured by, the apparatus 200.

Although not shown in the figures, in one embodiment the surgical staple remover 200 may include a miniature battery-powered LED on top of the opening 250 of housing 202, wherein the LED points at the service end of the apparatus 200 so as to illuminate the area surrounding the staple being removed. Alternatively, the LED may be placed on top of the arm 350, on top of the tip 352 of the arm 350 or under the opening 250 of housing 202.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of Applicant's surgical staple remover apparatus.

What is claimed is:

1. A surgical staple remover apparatus, comprising:
   a handle located at a rear of the apparatus;
   an upward sloped jaw element comprising a pair of parallel jaws;
   an arm having a hook element on a first end, wherein the arm is positioned such that the hook element is disposed over the jaw element;
   a pivot point located between the first end and a second end of the arm, such that the arm pivots about the pivot point;
   a lever mechanically coupled to the arm via a first beam and a second beam, wherein the first beam is rotatably coupled with the lever on a first end of the first beam and rotatably coupled with the second beam on a second end of the first beam, wherein the second beam is rotatably coupled to the arm, wherein moving the lever closer to the handle results in the arm pivoting about the pivot point, the hook element moving downwards towards the jaw element and the arm retracting toward the rear, thereby resulting in the hook element pressing against a crown of a surgical staple, deforming the surgical staple for removal and moving the surgical staple towards the rear; and
   a strip element located on top of the jaw element, such that when the hook element deforms and moves the surgical staple towards the rear, the surgical staple is moved under the strip element and held in place by same.

2. The surgical staple remover apparatus of claim 1, further comprising a housing having an interior volume that substantially encompasses the arm, the first beam and the second beam.

3. The surgical staple remover apparatus of claim 2, wherein the second beam is rotatably coupled to the housing at a first end of the second beam and rotatably coupled to the arm at a second end of the second beam.

4. The surgical staple remover apparatus of claim 3, wherein the second beam is rotatably coupled to the first beam at a location between the first and second ends of the second beam.

5. The surgical staple remover apparatus of claim 4, wherein the second end of the second beam includes an element that extends through a cutout in the arm.

6. The surgical staple remover apparatus of claim 5, further comprising an LED positioned on top of the housing and arranged so as to illuminate an area distal to the jaw element.

7. A surgical staple remover apparatus, comprising:
   a handle located at a rear of the apparatus;
   an upward sloped jaw element comprising a pair of parallel jaws;
   an arm having a hook element on a first end, wherein the arm is positioned such that the hook element is disposed over the jaw element;
   a pivot point located between the first end and a second end of the arm, such that the arm pivots about the pivot point;
   a lever mechanically coupled to the arm via a first beam and a second beam, wherein the first beam is rotatably coupled with the lever on a first end of the first beam and rotatably coupled with the second beam on a second end of the first beam, wherein the second beam is rotatably coupled to the arm, wherein moving the lever closer to the handle results in the arm pivoting about the pivot point, the hook element moving downwards towards the jaw element and the arm retracting toward the rear, thereby resulting in the hook element pressing against a crown of a surgical staple, deforming the surgical staple for removal and moving the surgical staple towards the rear;
   a strip element located on top of the jaw element, such that when the hook element deforms and moves the surgical staple towards the rear, the surgical staple is moved under the strip element and held in place by same; and
   a housing having an interior volume that substantially encompasses the arm, the first beam and the second beam.

* * * * *